United States Patent [19]

Vance

[11] Patent Number: 5,617,200
[45] Date of Patent: Apr. 1, 1997

[54] PULSE METHOD FOR MEASUREMENT OF RELATIVE SECONDARY PATH INTENSITIES IN OPTICAL WAVEGUIDE SYSTEMS

[75] Inventor: Miles E. Vance, Corning, N.Y.

[73] Assignee: Corning Incorporated, Corning, N.Y.

[21] Appl. No.: 579,417

[22] Filed: Dec. 27, 1995

[51] Int. Cl.$^6$ .................................................. G01N 21/88
[52] U.S. Cl. ......................................................... 356/73.1
[58] Field of Search ............................................ 356/73.1

[56] References Cited

PUBLICATIONS

Nigel G. Walker et al., "Polarization Control for Coherent Communications," *J. Lightwave Technology*, vol. 8, No. 3, Mar. 1990, 438–458.
Scott C. Rashleigh, "Origins and Control of Polarization Effects in Single–Mode Fibers," *J. Lightwave Technology*, vol. LT–1, No. 2, Jun. 1983 pp. 312–331.
R. Ulrich et al., "Bending–induced birefringence in single–mode fibers," *Optics Letters*, vol. 5, No. 6, Jun. 1980, pp. 273–275.
A. M. Smith, "Birefringence induced by bends and twists in single–mode optical fiber," *Applied Optics*, vol. 19, No. 15, Aug. 1980, 2606–2611.
R. Ulrich et al., "Polarization optics of twisted single–mode fibers," *Applied Optics*, vol. 28, No. 13, Jul. 1979, 2241–2251.
James L. Gimlett et al., "Effects of Phase–to–Intensity Noise Conversion by Multiple Reflections on Gigabit–per–Second DFB Laser Transmission Systems," *J. Lightwave Technology*, vol. 7, No. 6, Jun. 1989, 888–895.
H. Yoshinaga et al., "Influence of Reflected Light on Erbium–Doped Fiber Amplifiers for Optical AM Video Signal Transmission Systems," *J. Lightwave Technology*, vol. 10, No. 8, Aug. 1992, 1132–1136.

W. I. Way et al., "Multiple–Reflection–Induced Intensity Noise Studies in a Lightwave System foir Multichannel AM–VSB Television Signal Distribution," *IEEE Photonics Technology Letters*, vol. 2, No. 5, May 1990, 360–362.
Daniel A. Fishman et al., "Measurements and Simulation of Multipath Interference for 1.7 Gb/s Lightwave Transmission Systems Using single–and Multifrequency Lasers," *J. Lightwave Technology*, vol. 8, No. 6, Jun. 1990, 894–905.
M. Kobayashi et al., "Power Penalgy Due to Optical Reflections in Erbium–Doped Fiber Preamplifier," *IEEE Photonics Technology Lett.*, vol. 5, No. 8, Aug. 1993, 925–928.
A. D. Kersey et al., "Optimization and Stabilization of Visibility in Interferometric Fiber–Optic Sensors Using Input–Polarization Control," *J. Lightwave Technology*, vol. 6, No. 110, Oct. 1988, 1599–1609.
R. A. Bergh et al., "Single–mode fiber–optic polarizer," *Optics Letters*, vol. 5, No. 11, Nov. 1980, 479–481.
Michael J. Marrone et al, "Fiber in–line polarizaiton rotator and mode interchanger," *Applied Optics*, vol. 26, No. 16, Aug. 1987, 3194–3195.

*Primary Examiner*—Vincent P. McGraw
*Attorney, Agent, or Firm*—Maurice M. Klee; William Greener

[57] ABSTRACT

A method for measuring the secondary path intensity of an optical unit, such as an optical amplifier, is provided. The method includes applying a pulse of light to a first end of the unit and detecting the light exiting from the second end of the unit. The exiting light is analyzed to determine a primary pulse intensity and a secondary pulse intensity which preferably includes the effects of Rayleigh backscattering (RBS). The ratio of the secondary pulse intensity to the primary pulse intensity provides an accurate measure of the unit's secondary path intensity.

13 Claims, 2 Drawing Sheets

PULSE METHOD FOR MEASUREMENT OF RELATIVE SECONDARY PATH INTENSITIES IN OPTICAL WAVEGUIDE SYSTEMS

FIELD OF THE INVENTION

This invention relates to methods and apparatus for measuring relative secondary path intensities ($\alpha_I$ values) which produce interferometric phase-to-intensity noise in optical waveguide systems and, in particular, to the measurement of such values for systems which include optical amplifiers.

BACKGROUND OF THE INVENTION

Interferometric phase-to-intensity noise is generated in optical fiber communication systems when a small spurious delayed secondary fraction of the optical signal is combined with the primary optical signal at the receiver. See James L. Gimlett and Nim K. Cheung, *J. Lightwave Technology*, Vol. 7, No. 6, June 1989, 888–895. Because of phase fluctuations of the laser source, the interference of these two waves is time-dependent, producing intensity noise on the signal.

For example, when two small reflectances $R_1$ and $R_2$ at points along an optical fiber allow signal light to be doubly reflected between them, the doubly-reflected light is time-delayed and continues in the same direction as the direct light. The original signal and the doubly-reflected light are thus capable of interfering with one another to produce intensity noise. This noise contribution is especially strong when the delay time is greater than the coherence time of the source laser. The effect is further exacerbated in systems containing optical amplifiers when a gain element lies between the reflectances. See Hisao Yoshinaga, Koji Kikushima, and Etsugo Yoneda, *J. Lightwave Technology*, Vol. 10, No. 8, Aug. 1992, 1132–1136. This is especially so when the secondary signal is amplified more than the primary signal.

In both analog and digital optical systems, acceptable limits on optical isolation and reflections from connectors and other components are dictated by this interferometric phase-to-intensity noise effect. See Gimlett et al., supra; Yoshinaga et al., supra; W. I. Way, C. Lin, C. E. Zah, L. Curtis, R. Spicer, and W. C. Young, *IEEE Photonics Technology Lett.*, Vol. 2, No. 5, May 1990, 360–362; Daniel A. Fishman, Donald G. Duff, and Jonathan A. Nagel, *J. Lightwave Technology*, Vol. 8, No. 6, June 1990, 894–905; and M. Kobayashi, T. Ishihara, and M. Gotoh, *IEEE Photonics Technology Lett.*, Vol. 5, No. 8, Aug. 1993, 925–928.

The magnitude and electrical frequency dependence of this noise depend upon the relative secondary path intensities ($\alpha_I$), the time delay, and the optical spectrum of the source. Quantitatively, for cases where the laser source has a Lorentzian line shape and where the time delay of the secondary path exceeds the source coherence time, the frequency-dependent contribution to the noise factor caused by interferometric phase-to-intensity noise ($F_{INT}(f)$) is given by:

$$F_{INT}(f) = \frac{4\alpha_I}{\pi} \cdot \left[ \frac{\Delta v}{(\Delta v)^2 + f^2} \right] \cdot \frac{P_i}{2hv} \qquad (1)$$

where f is the electrical frequency at which the noise measurement is made, v is optical frequency of the source, $\Delta v$ is the optical linewidth of the source, h is Planck's constant, and $P_i$ is the optical input power to the secondary path. See Gimlett et al., supra, and Yoshinaga et al., supra.

For an optical circuit of the type shown in FIG. 1, $$\alpha_I = R^2_{EFF} = G_f G_b R_1 R_2 \qquad (2)$$

where $R_1$ and $R_2$ are effective optical power reflectances, $R_1$ representing the combined effect of all reflectors located before the gain fiber G and $R_2$ representing the combined effect of all reflectors located after the gain fiber. For example, $R_2$ includes the localized reflectance $R_2$ and the distributed gain-fiber Rayleigh backscattering (RBS) equivalent reflectance $R_{RBS}$, which conceptually is shown as being located after the gain fiber in FIG. 1. Thus, $$R_2 = R_2' + R_{RBS} \qquad (3)$$

Normally, for steady state conditions, the forward gain $G_f$ and the backward gain $G_b$ are the same, but these gains could be significantly different if, for example, an optical isolator were located between $R_1$ and $R_2$.

While it might be possible to measure all of the relative secondary path intensities ($\alpha_I$) and delay times within an optical amplifier unit (or other optical unit) during construction, it is desirable to determine $\alpha_I$ by means of external measurements on the amplifier considered as a unit. Once this $\alpha_I$ is known, it becomes possible to calculate the interferometric noise which would be produced in specific systems employing the amplifier. The present invention is directed to providing such an external measurement of $\alpha_I$ for optical amplifiers and other optical units.

SUMMARY OF THE INVENTION

In accordance with the invention, the relative secondary path intensity of an optical unit, e.g., an amplifier unit, is determined by:

(a) applying a pulse of light from a light source, e.g., a laser, to a first end of the unit;

(b) detecting the intensity of the light at the second end of the unit as a function of time using a detector;

(c) identifying a first time segment of the detected light and a second time segment of the detected light, the second time segment being later in time than the first time segment;

(d) determining a first optical energy for the first time segment;

(e) determining a second optical energy for the second time segment; and (f) determining the ratio of the second optical energy to the first optical energy.

The ratio determined in step (f) is an accurate measure of the desired relative secondary path intensity ($\alpha_I$) of the optical unit when $\alpha_I \ll 1$.

In certain embodiments of the invention, the state of polarization (SOP) of the light pulse is adjusted prior to being applied to the first end of the unit under test to minimize the effects of polarization dependent loss on the $\alpha_I$ measurement.

Figure 1:
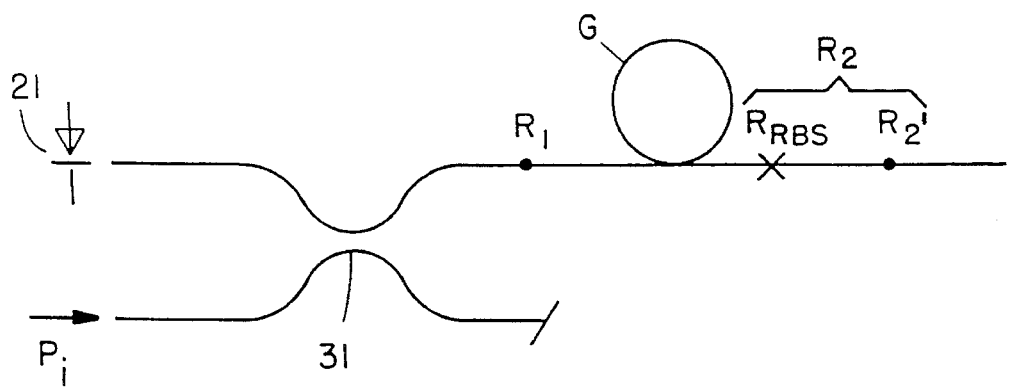
FIG. 1 is a schematic diagram of an optical amplifier whose relative secondary path intensity can be determined using the method of the invention.

The foregoing drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention. The drawings are not intended to indicate scale or relative proportions of the elements shown therein.

The reference numbers used in the drawings correspond to the following:

11 pulsed laser
13 optical fiber amplifier under test
15 optical isolator
17 polarization controller
19 WDM coupler
21 pump laser
23 optical isolator
25 receiver photodiode
27 preamplifier
29 oscilloscope
31 coupler
33 optical isolator
35 optical isolator

DESCRIPTION OF THE PREFERRED EMBODIMENTS

An examination of FIG. 1 and of equation 2 above shows that the quantity $R^2_{EFF}$ is the net gain experienced by the doubly reflected wave as compared to the net gain experienced by the direct wave, i.e., it is the ratio of the doubly reflected power to the direct power when the two waves recombine. This concept, which forms the basis of the present invention, also applies to more complicated amplifier configurations and/or combinations of amplifiers which produce delayed waves taking paths parallel to the direct path. The variable $\alpha_I$ describes this more general case.

As discussed above, the greatest interferometric noise occurs when the delay time exceeds the laser coherence time, a condition which is generally satisfied for the relatively long delays which occur in fiber optic systems and amplifiers. Typical delay times associated with fiber optic amplifiers are hundreds of nanoseconds produced by double reflection between reflectances which are separated by tens of meters of optical fiber. An input signal pulse of a few nanoseconds duration thus produces a secondary pulse which can be distinguished temporally from the primary pulse at the output of the fiber amplifier. In accordance with the invention, these two pulses are used to determine $\alpha_I$ values.

Figure 2:
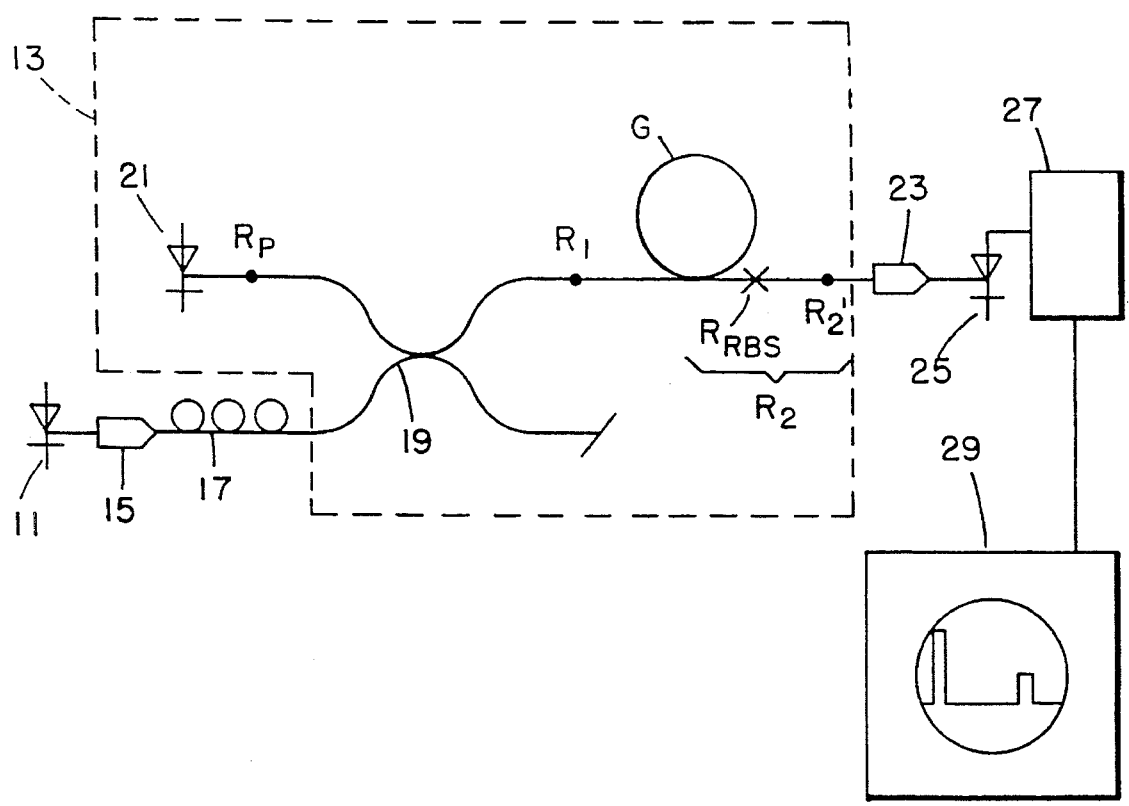
FIG. 2 is a schematic diagram of suitable apparatus for practicing the method of the invention.

FIG. 2 shows suitable apparatus for practicing the invention to measure an $\alpha_I$ value for a fiber optic amplifier 13. Amplifier 13 includes pump laser 21, WDM coupler 19, and gain fiber G. As in FIG. 1, $R_1$ represents a small localized reflection before the gain fiber, $R_2'$ represents a similar reflection after the gain fiber, and RBS represents the distributed Rayleigh backscattering from the gain fiber and connecting fibers. The apparatus of FIG. 2 can, of course, be used to measure $\alpha_I$ values for optical units other than optical amplifiers by simply connecting the unit to be tested in place of amplifier 13.

As shown in FIG. 2, the test apparatus comprises pulsed laser 11, optical isolators 15 and 23, receiver photodiode 25, preamplifier 27, and oscilloscope 29. Typically, pulsed laser 11 will have a coherence time which is less than the time required for the pulse of light to travel from the first end to the second end of the unit under test. The apparatus as shown in FIG. 2 also includes polarization controller 17, the function of which is discussed below.

In operation, pulsed laser 11 produces a pulse of light which passes through the unit (amplifier) under test and is detected by receiver photodiode 25. Part of the input light is also doubly reflected by $R_1$ and $R_2$, and that doubly reflected light is also detected by receiver photodiode 25. Pulsed laser 11 has a coherence time which is less than the time required for a pulse of light to travel from the input end to the output end of the unit under test.

Figure 3:
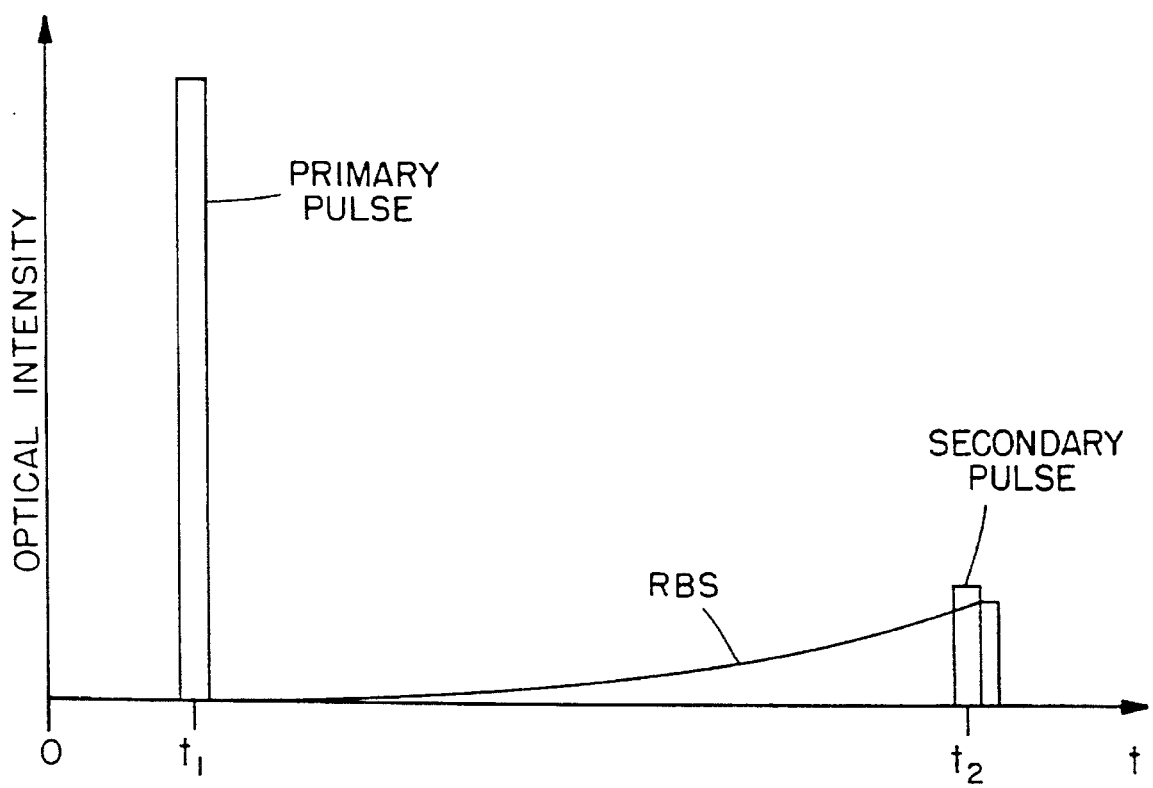
FIG. 3 is a schematic diagram illustrating the type of trace which is observed on oscilloscope 29 of FIG. 2 when the method of the invention is practiced.

FIG. 3 schematically shows the time trace which is observed on oscilloscope 29 for a single input pulse from pulsed laser 11. Two distinct pulses occurring in two separate time segments of the trace, i.e., the primary pulse and the secondary pulse, are evident in this figure. The weak secondary pulse occurs at the delay time $t_2-t_1$ required for the secondary wave to travel from $R_2$ to $R_1$ and back to $R_2$.

FIG. 3 also shows the optical intensity produced by Rayleigh backscattering (RBS). It should be noted that for purposes of illustration, the magnitude of the RBS trace has been greatly exaggerated in FIG. 3.

As can be seen in FIG. 3, the RBS intensity, which results from Rayleigh scattering of the primary pulse and subsequent reflection at $R_1$, increases exponentially, reaching a maximum at time $t_2$. Its contribution to the unit's $\alpha_I$ value is most conveniently included in the measurement process by integrating the detected optical intensities over time to get relative pulse energies. It should be noted that the use of such an energy ratio is an appropriate approach for including the effects of RBS because, in a continuous wave optical transmission system, the RBS optical power from each element of fiber length adds linearly to the electrical noise power.

The first time segment for which an optical energy is determined can be, for example, for times centered on and in the immediate vicinity of $t_1$, while the second time segment can begin at, for example, the midpoint of $t_1$ and $t_2$ and continue through $t_2$. The optical energy for the first segment is simply the integral over the time segment surrounding $t_1$. The optical energy for the second segment is preferably an integral over that time segment. In this way, the effect of RBS is included in the optical energy value for the second time segment. Other approaches for determining time segments and optical energies or intensities can, of course, be used if desired.

Once the two energy values have been determined, the $\alpha_I$ value for the unit is determined by computing the ratio of the optical energy for the second time segment to the optical energy for the first time segment.

Precision of the relative energy measurement can be increased by utilizing trains of pulses and averaging the responses obtained for the various pulses. The averaging can be performed by determining average energy values for the first and second time segments for the various pulses and then computing the ratio of those average energies, or the averaging can be performed by determining an energy ratio for each pulse and then averaging those ratios.

Enhancement of the secondary pulse energy can be attained by inserting a known relatively large partial reflectance, for example 50%, either before or after the unit (amplifier) under test. Placed after the amplifier, a known large reflectance allows calculation of the value of $R_1$. Placed before the amplifier, it allows evaluation of $R_{RBS}$ and $R_2'$.

As discussed above, the apparatus of FIG. 2 can include polarization controller 17. A discussion of polarization controllers can be found in, for example, N. G. Walker and G. R. Walker, *J. Lightwave Technology*, Vol. 8, No. 3, March 1990, 438–458; and A. D. Kersey, M. J. Marrone, A. Dandridge, and A. B. Tveten, *J. Lightwave Technology*, Vol. 6, No. 10, October 1988, 1599–1609. The role of polarization in the measurement system of the invention can be understood as follows.

Equation 1 above is based on the assumption that the delayed wave and the direct wave have the same state of polarization (SOP), thus producing maximum interference. See Gimlett et al., supra. Because of birefringence of the optical fiber this will not in general be the case. This result can be understood by consideration of the polarization eigenmodes of the unit under test. See Scott C. Rashleigh, *J. Lightwave Technology*, Vol. LT-1, No. 2, June, 1983, 312–331.

A polarization eigenmode is a SOP which does not change as the wave propagates through the system. For the optical system of FIG. 1, the simplest case occurs when (1) $R_{RBS}=0$, (2) the reflections exhibit no polarization dependence, and (3) the coiled fiber exhibits only linear birefringence. In that case, the two mutually orthogonal eigenmodes are (1) linear polarization along the fast birefringence axis of the fiber and (2) linear polarization along the slow axis.

Adjustment of the input SOP so that the SOP of the primary wave at $R_2'$ matches either of these eigenmodes results in a secondary wave which propagates with unchanging polarization along the path $R_2'R_1R_2'$, producing maximum interference at $R_2'$. This is a global maximum, being independent of the optical path length between $R_1$ and $R_2'$ and thus is independent of the fiber beat length, which depends on the temperature and stress distribution within the fiber. See A. M. Smith, *Applied Optics*, Vol. 19, No. 15, Aug. 1980, 2606–2611; and R. Ulrich, S. C. Rashleigh, and W. Eikhoff, *Optics Letters*, Vol. 5, No. 6, June 1980, 273–275. This eigenmode analysis can be generalized to include elliptical birefringence as well as physical twist of the fiber. See Rashleigh, supra; and R. Ulrich and A. Simon, *Applied Optics*, Vol. 18, No. 13, 1 Jul. 1979, 2241–2251.

Furthermore, if $R_{RBS}\neq 0$, Rayleigh backscattering contributions to the interferometric noise are maximized by the same input SOP that maximizes the contribution of point reflectances. This holds true as long as the path difference between the primary and secondary waves is near or greater than the source coherence length but is not great enough to depolarize the RBS. Under these conditions, the guided portion of the backscattered wave from a given location along the fiber is coherent with and has essentially the same SOP as the primary wave incident at that point. Thus, when the input SOP is adjusted to be an eigenmode of the system, all the waves, primary, secondary, and RBS secondary, maintain the same SOP and produce maximum interference.

The foregoing discussion of the effects of polarization applies to the magnitude of the interference between the primary and secondary waves. Since the present invention does not rely on such interference, the complications arising from those effects are automatically avoided by the technique of the invention. There is, however, a polarization effect, namely, polarization dependent loss (PDL), which can affect the $\alpha_I$ values determined in accordance with the invention.

When there is no PDL, the relative pulse energies do not depend upon polarization. However, if there is PDL, as might be the case for pump reflectance $R_p$ in FIG. 2, combined with the PDL of coupler 19, the secondary pulse energy is polarization dependent. More generally, if PDL exists within the delay path, the magnitudes of the secondary pulse, the primary pulse, or both, become dependent on the SOP of the input wave.

Figure 4:
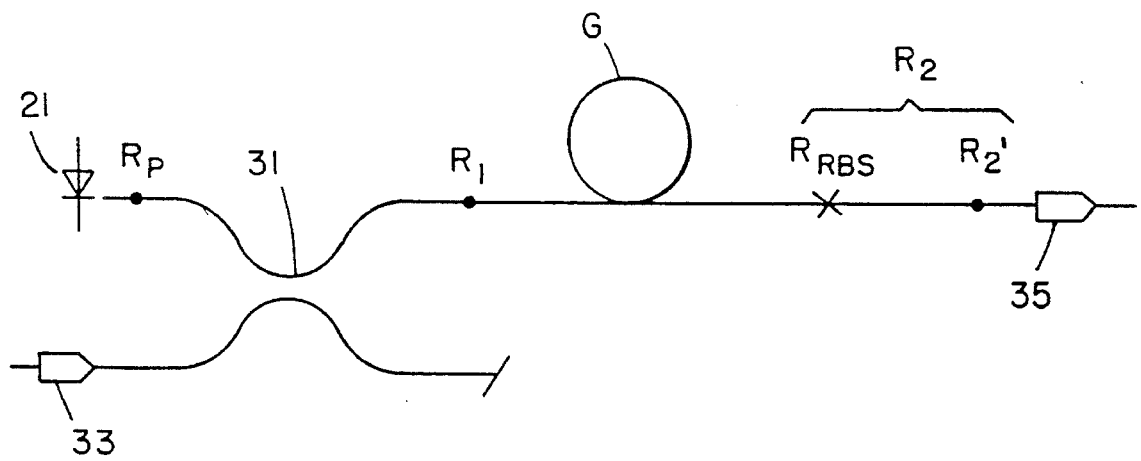
FIG. 4 is a schematic diagram of an optical amplifier system which exhibits polarization dependent loss (PDL).

For example, consider the amplifier configuration shown in FIG. 4, which for purposes of illustration will be assumed to comprise an erbium fiber and to be operated at 1542 nm. Part of the reflectance denoted $R_1$ is known to be produced when 1542 nm reflected signal light proceeds from the erbium fiber G through the high loss leg of the coupler 31 to the pump 21, which reflects a small portion $R_p$ back through coupler 31 toward the erbium fiber G. A typical coupler 31 will have a PDL of the order of 3 dB for 1542 nm light transmitted through this path. Additional contributions to $R_1$ are made by reflection from coupler 31 and reflection from optical isolator 33. Reflectance $R_2$ is provided by reflection from optical isolator 35 and RBS from the gain fiber and any other fiber between $R_1$ and $R_2'$.

The magnitude of the secondary pulse arising from reflection from coupler 31 and isolator 33 is independent of polarization and fiber birefringence and is the maximum attainable value.

On the other hand, the magnitude of the secondary pulse arising from pump reflection depends on the input SOP, the azimuth of the coupler PDL, and the azimuths of the polarization eigenmodes of the fiber between the coupler and the pump. Adjustment of the input SOP can in general produce two different maxima in the secondary pulse magnitude, depending on the alignment of the PDL azimuth with the eigenmodes of the coupler-pump path. When the low-PDL (highest transmittance) azimuth is aligned with an eigenmode of the coupler-pump path and the input SOP is adjusted to agree with that eigenmode, the highest maximum secondary pulse is attained; when the input SOP is adjusted to agree with the other eigenmode, the lowest maximum secondary pulse is attained and is reduced by the total double-pass PDL of the coupler. When the low-PDL azimuth is not aligned with an eigenmode of the coupler-pump path, the heights of the two maxima differ less from each other and fall between the highest and lowest maxima for the aligned case. In either case, the magnitudes of these maxima are temperature-independent.

Thus, the method of the present invention can give a worst-case value of the effective $\alpha_I$ for an optical amplifier when the maximization of the interferometric noise is subject to the constraint that the input SOP is adjusted so that the SOP at $R_2$ is identical to an eigenmode of the $R_1R_2$ path. In practice, when significant PDL exists or is expected to exist in a unit under test, polarization controller 17 is adjusted to produce a maximum secondary pulse. In this way, a worse-case $\alpha_I$ value for the unit is obtained.

The determination of the optical energies for the first and second time segments, as well as the calculation of $\alpha_I$ values from those energies, can be performed manually using a trace of the type shown in FIG. 3 or can be automated using conventional data acquisition equipment and a suitably programmed computer, e.g., a personal computer, to analyze the data. The automated approach is especially preferred when multiple pulses are used to obtain an $\alpha_I$ value.

The measurement technique of the invention has numerous advantages including: 1) the technique can be readily implemented using conventional, widely-available equipment; 2) the $\alpha_I$ values determined by the technique are generally insensitive to temperature effects; 3) as discussed above, when there is no polarization dependent loss, the relative pulse energies, and thus the $\alpha_I$ values determined therefrom, do not depend upon polarization; and 4) even when there is polarization dependent loss, the technique is relatively insensitive to fiber birefringence.

Although preferred and other embodiments of the invention have been described herein, further embodiments may be perceived by those skilled in the art without departing from the scope of the invention as defined by the following claims.

What is claimed is:

1. A method for measuring the relative secondary path intensity of an optical unit, said unit having a first end and a second end, said method comprising:

(a) applying a pulse of light from a light source to the first end of the unit;

(b) detecting the intensity of the light at the second end of the unit as a function of time using a detector;

(c) identifying a first time segment of the detected light and a second time segment of the detected light, the second time segment being later in time than the first time segment;

(d) determining a first optical energy for the first time segment;

(e) determining a second optical energy for the second time segment; and (f) determining the ratio of the second optical energy to the first optical energy, said ratio being indicative of the relative secondary path intensity of the optical unit.

2. The method of claim 1 wherein steps (d) and (e) comprise integrating the intensity of the detected light over the first and second time segments, respectively.

3. The method of claim 1 wherein multiple pulses are used and the ratio of step (f) represents an average over the multiple pulses.

4. The method of claim 1 comprising the additional step, prior to step (a), of placing a reflectance between the light source and the first end of the unit.

5. The method of claim 1 comprising the additional step, prior to step (a), of placing a reflectance between the second end of the unit and the detector.

6. The method of claim 1 including the additional step, prior to step (a), of adjusting the state of polarization of the light pulse.

7. The method of claim 6 wherein the state of polarization is adjusted to maximize the second optical energy.

8. The method of claim 1 where the unit is an optical amplifier.

9. Apparatus for measuring the relative secondary path intensity of an optical unit, said unit having a first end and a second end, said apparatus comprising:

(a) a light source for applying a pulse of light to the first end of the unit;

(b) a detector for detecting the intensity of the light at the second end of the unit as a function of time;

(c) means for determining first and second optical energies for first and second time segments of the detected light, the second time segment being later in time than the first time segment; and (d) means for determining the ratio of the second optical energy to the first optical energy, said ratio being indicative of the relative secondary path intensity of the optical unit.

10. The apparatus of claim 9 further comprising a reflectance between the light source and the first end of the unit.

11. The apparatus of claim 9 further comprising a reflectance between the second end of the unit and the detector.

12. The apparatus of claim 9 further comprising means for adjusting the state of polarization of the light pulse.

13. The apparatus of claim 12 wherein the means for adjusting the state of polarization of the light pulse is located between the light source and the first end of the unit.

* * * * *